United States Patent
Sohn et al.

(10) Patent No.: US 8,759,763 B2
(45) Date of Patent: Jun. 24, 2014

(54) METHOD AND APPARATUS TO MEASURE STEP HEIGHT OF DEVICE USING SCANNING ELECTRON MICROSCOPE

(71) Applicant: Samsung Electronics Co., Ltd, Suwon-si, Gyeonggi-do (KR)

(72) Inventors: Young-Hoon Sohn, Seongnam-si (KR); Jin-Woo Lee, Seongnam-si (KR); Yong-Deok Jeong, Hwaseong-si (KR); Yu-Sin Yang, Seoul (KR); Sang-Kil Lee, Yongin-si (KR); Chung-Sam Jun, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 13/680,347

(22) Filed: Nov. 19, 2012

(65) Prior Publication Data

US 2013/0234021 A1 Sep. 12, 2013

(30) Foreign Application Priority Data

Mar. 7, 2012 (KR) .................. 10-2012-0023458

(51) Int. Cl.
*G01B 15/00* (2006.01)
*G01N 23/225* (2006.01)
*H01J 37/26* (2006.01)

(52) U.S. Cl.
CPC .............. *G01B 15/00* (2013.01); *G01N 23/225* (2013.01); *H01J 2237/2815* (2013.01); *H01J 37/26* (2013.01)
USPC ........... 250/307; 250/306; 250/310; 250/311; 250/396 R; 250/396 ML; 850/10; 382/168; 382/169

(58) Field of Classification Search
CPC .................. G02B 21/006; H01J 2237/281
USPC .......... 250/307, 310, 396 R, 396 ML; 850/10
See application file for complete search history.

(56) References Cited

U.S. PATENT DOCUMENTS

| 4,748,335 A * | 5/1988 | Lindow et al. ........... 250/559.22 |
| 7,365,325 B2 | 4/2008 | Miyamoto et al. |
| 2008/0175466 A1 * | 7/2008 | Ishikawa ....................... 382/141 |
| 2008/0267489 A1 * | 10/2008 | Xiao et al. ..................... 382/147 |
| 2008/0283766 A1 * | 11/2008 | Inokuchi ................... 250/396 R |

FOREIGN PATENT DOCUMENTS

| JP | 06-076778 | 3/1994 |
| JP | 2008-211087 | 11/2008 |

(Continued)

*Primary Examiner* — Nicole Ippolito
*Assistant Examiner* — Kevin Chung
(74) *Attorney, Agent, or Firm* — Stanzione & Kim, LLP

(57) ABSTRACT

A method of measuring a step height of a device using a scanning electron microscope (SEM), the method may include providing a device which comprises a first region and a second region, wherein a step is formed between the first region and the second region, obtaining a SEM image of the device by photographing the device using a SEM, wherein the SEM image comprises a first SEM image region for the first region and a second SEM image region for the second region, converting the SEM image into a gray-level histogram and calculating a first peak value related to the first SEM image region and a second peak value related to the second SEM image region, wherein the first peak value and the second peak value are repeatedly calculated by varying a focal length of the SEM, and determining a height of the step by analyzing a trend of changes in the first peak value according to changes in the focal length and a trend of changes in the second peak value according to the changes in the focal length.

19 Claims, 13 Drawing Sheets

(56) References Cited

FOREIGN PATENT DOCUMENTS

| | | |
|---|---|---|
| JP | 2010-087075 | 4/2010 |
| JP | 2010-225812 | 7/2010 |
| JP | 2010-232434 | 10/2010 |
| KR | 2000-0015472 | 3/2000 |
| KR | 2000-0020607 | 4/2000 |
| KR | 10-2006-0070003 | 6/2006 |
| KR | 10-2008-0102648 | 11/2008 |

* cited by examiner

METHOD AND APPARATUS TO MEASURE STEP HEIGHT OF DEVICE USING SCANNING ELECTRON MICROSCOPE

CROSS-REFERENCE TO RELATED APPLICATIONS

This application claims priority from Korean Patent Application No. 10-2012-0023458 filed on Mar. 7, 2012 in the Korean Intellectual Property Office, the disclosure of which is incorporated herein by reference in its entirety.

BACKGROUND OF THE INVENTION

1. Field of the Invention

The present inventive concept relates to a method and apparatus to measure a step height of a device using a scanning electron microscope (SEM).

2. Description of the Related Art

As semiconductor devices become smaller, the processing margin for forming fine patterns is being reduced. Specifically, the processing margin for the size of pitches of fine patterns as well as the processing margin for etch depths of the fine patterns are being reduced. Therefore, a technology for measuring a 2D critical dimension (CD) to measure a pitch of a fine pattern and a technology for measuring a 3D depth with precision to measure an etch depth of the fine pattern are required.

To measure etch depths of fine patterns, an atomic force microscope (AFM) or optical CD measurement equipment can be used.

The AFM measures an etch depth of a fine pattern using a contact-scanning method that utilizes a probe tip. Therefore, as the number of times that the AFM measures an etch depth of a fine pattern increases, the probe tip of the AFM may wear down, leading to a reduction in measurement reliability.

On the other hand, the OCD measurement equipment theoretically models and calculates light-scattering characteristics of a fine pattern to measure the 3D shape of the fine pattern. The OCD measurement equipment uses a non-contact scanning method. However, the OCD measurement equipment can measure the 3D shape of a fine pattern through calculation only when the fine pattern is uniformly repeated within a spot of light used.

SUMMARY OF THE INVENTION

Features of the present inventive concept provide a method of measuring a step height of a device using a scanning electron microscope (SEM) which can measure a 2D critical dimension (CD), the method being a technology of measuring a 3D etch depth of a fine pattern using a non-contact scanning method regardless of the repeatability or shape of the fine pattern.

Additional features and utilities of the present general inventive concept will be set forth in part in the description which follows and, in part, will be obvious from the description, or may be learned by practice of the general inventive concept.

Exemplary embodiments of the present inventive concept provide a method of measuring a step height of a device using a scanning electron microscope (SEM), the method including providing a device which comprises a first region and a second region, wherein a step is formed between the first region and the second region, obtaining a SEM image of the device by photographing the device using a SEM, wherein the SEM image comprises a first SEM image region for the first region and a second SEM image region for the second region, converting the SEM image into a gray-level histogram and calculating a first peak value related to the first SEM image region and a second peak value related to the second SEM image region, wherein the first peak value and the second peak value are repeatedly calculated by varying a focal length of the SEM, and determining a height of the step by analyzing a trend of changes in the first peak value according to changes in the focal length and a trend of changes in the second peak value according to the changes in the focal length.

Exemplary embodiments of the present inventive concept also provide an apparatus to measure a height of a step formed between a first region and a second region of a device by using a SEM, the apparatus including: a SEM image acquisition unit to obtain a SEM image which comprises a first SEM image region for the first region and a second SEM image region for the second region, wherein the SEM image is repeatedly captured by varying a focal length of the SEM multiple times, a histogram generation unit converting the SEM image into a gray-level histogram, a peak value calculation unit to calculate a first peak value related to the first SEM image region and a second peak value related to the second SEM image region by analyzing the gray-level histogram, a trend analysis unit to analyze a trend of changes in the first peak value according to changes in the focal length and a trend of changes in the second peak value according to the changes in the focal length, and a step height determination unit to receive an analysis result from the trend analysis unit and determining the height of the step.

Exemplary embodiments of the present inventive concept also provide a method of measuring a difference in height of a device using a scanning electron microscope (SEM), the method including obtaining an SEM image of a device by photographing the device using an SEM, wherein the SEM image comprises a first SEM image region for a first region of the device and a second SEM image region for a second region of the device; converting the SEM image into a gray-level histogram and calculating a first peak value related to the first SEM image region and a second peak value related to the second SEM image region, wherein the first peak value and the second peak value are repeatedly calculated by varying a focal length of the SEM; and determining a difference in height between the first region and the second region by analyzing a trend of changes in the first peak value according to changes in the focal length and a trend of changes in the second peak value according to the changes in the focal length.

In an exemplary embodiment, the first region of the device is stepped with respect to the second region of the device.

Exemplary embodiments of the present inventive concept also provide a method of measuring a difference in height of a device using a scanning electron microscope (SEM), the method including obtaining an SEM image of a device by photographing the device using an SEM, wherein the SEM image comprises a first SEM image region for a first region of the device and a second SEM image region for a second region of the device; calculating a first peak value related to the first SEM image region and a second peak value related to the second SEM image region, wherein the first peak value and the second peak value are repeatedly calculated by varying a focal length of the SEM; and determining a a difference in height between the first region and the second region by analyzing a trend of changes in the first peak value according to changes in the focal length and a trend of changes in the second peak value according to the changes in the focal length.

The method may further include converting the obtained SEM image into a gray-level histogram, wherein the first peak value is a gray-level value corresponding to a peak related to the first SEM image region in the gray-level histogram, and the second peak value is a gray-level value corresponding to a peak related to the second SEM image region in the gray-level histogram.

The method may further include converting the obtained SEM image into a gray-level histogram, wherein the first peak value is a frequency value corresponding to the peak related to the first SEM image region in the gray-level histogram, and the second peak value is a frequency value corresponding to the peak related to the second SEM image region in the gray-level histogram.

In an exemplary embodiment, the first region of the device is stepped with respect to the second region of the device.

BRIEF DESCRIPTION OF THE DRAWINGS

These and/or other features and utilities of the present general inventive concept will become apparent and more readily appreciated from the following description of the embodiments, taken in conjunction with the accompanying drawings of which.

DETAILED DESCRIPTION OF THE PREFERRED EMBODIMENTS

Figure 1:
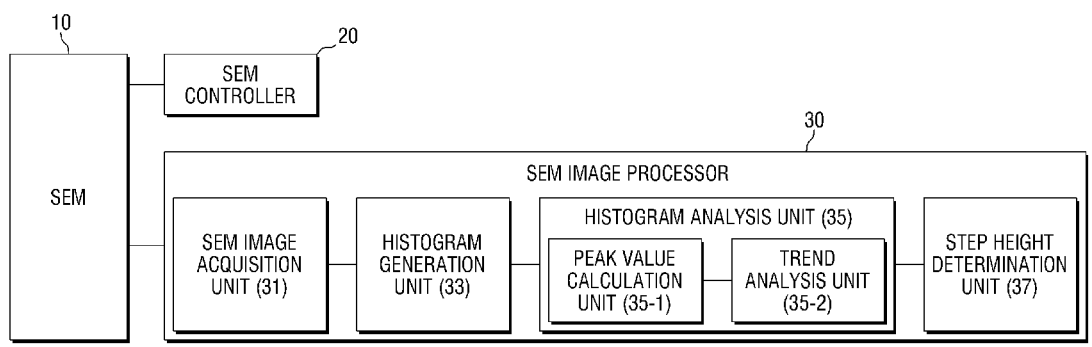
FIG. 1 is a block diagram of an apparatus to measure a step height according to embodiments of the present inventive concept.

Features and utilities of the present inventive concept and methods of accomplishing the same may be understood more readily by reference to the following detailed description of preferred embodiments and the accompanying drawings. The present inventive concept may, however, be embodied in many different forms and should not be construed as being limited to the embodiments set forth herein. Rather, these embodiments are provided so that this disclosure will be thorough and complete and will fully convey the concept of the inventive concept to those skilled in the art, and the present inventive concept will only be defined by the appended claims. In the drawings, the thickness of layers and regions are exaggerated for clarity.

It will be understood that when an element or layer is referred to as being "connected to," or "coupled to" another element or layer, it can be directly connected to or coupled to another element or layer or intervening elements or layers may be present. In contrast, when an element is referred to as being "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present inventive concept.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

An apparatus to measure a step height according to an embodiment of the present inventive concept will now be described with reference to FIG. 1. FIG. 1 is a block diagram of an apparatus 1 to measure a step height according to embodiments of the present inventive concept.

Referring to FIG. 1, the apparatus 1 to measure a step height may include, but is not limited to, a scanning electron microscope (SEM) 10, a SEM controller 20, and a SEM image processor 30. The step height measuring apparatus 1 uses the SEM 10 which is an inspection device using an electron beam. Specifically, the step height measuring apparatus 1 may measure a step height of a device 100 (see FIG. 3) by analyzing a SEM image 200 (see FIG. 4) obtained from the SEM 10.

The SEM 10 may be an inspection region which scans the device 100 with electrons. For example, the SEM 10 may include, but is not limited to, an electron beam source which generates an electron beam, an electromagnetic lens which focuses the electron beam, and a stage on which an inspection target is placed.

To measure a step height using the step height measuring apparatus 1, the SEM image 200 may be captured by changing a position at which a focus of the SEM 10 is formed by adjusting a focal length of the SEM 10. In the present specification, the position at which the focus of the SEM 10 is formed may denote a position at which a focus of an electron beam of the SEM 10 is formed. In addition, adjusting the focal length of the SEM 10 may denote adjusting a focal length of the electromagnetic lens of the SEM 10.

The SEM controller 20 may be a control region which controls the SEM 10. For example, the SEM controller 20 may adjust the focal length of the SEM 10 in order to change the position at which the focus of the SEM 10 is formed.

The SEM image processor 30 may be a portion of the step height measuring apparatus 1 which determines the step height of the device 100 by analyzing the SEM image 200 obtained through electron scanning by the SEM 10. Specifically, the SEM image processor 30 may include a SEM image acquisition unit 31, a histogram generation unit 33, a histogram analysis unit 35, and a step height determination unit 37.

The SEM image acquisition unit 31 may be a portion of the SEM image processor 30 which obtains the SEM image 200 by detecting secondary electrons emitted from the inspection region by electron beam scanning. That is, the SEM image acquisition unit 31 may obtain the SEM image 200 of an inspection target such as the device 100. The SEM image 200 may be a 2D image and may be captured by changing the focal length of the SEM 10 multiple times.

The histogram generation unit 33 is a portion of the SEM image processor 30 which generates a gray-level histogram based on the SEM image 200 obtained by the SEM image acquisition unit 31. That is, the histogram generation unit 33 may convert the SEM image 200 into a gray-level histogram.

The gray-level histogram represents the distribution of brightness values of a plurality of pixels included in the SEM image 200. For example, a 256 gray-level SEM image may have a brightness value range of 0 to 255 and may be converted into a gray-level histogram in which the frequency of each brightness value is represented by the height of a graph. Here, the gray levels are not limited to the 256 gray levels.

The histogram analysis unit 35 is a portion of the SEM image processor 30 which analyzes characteristics of a gray-level histogram generated by the histogram generation unit 33. The histogram analysis unit 35 may include a peak value calculation unit 35-1 and a trend analysis unit 35-2.

The peak value calculation unit 35-1 may calculate a peak value of a gray-level histogram. A peak denotes a point at which frequency has a maximum value in a gray-level histogram. In addition, a peak value may be any one of a gray-level value and a frequency value at a peak.

The trend analysis unit 35-2 may analyze a trend of changes in a peak value according to changes in the focal length of the SEM 10. The trend analysis unit 35-2 may receive information about a focal length of the SEM 10 and a peak value corresponding to the focal length from the peak value calculation unit 35-1. Specifically, the trend analysis unit 35-2 may receive information about various peak values corresponding respectively to various focal lengths of the SEM 10 from the peak value calculation unit 35-1. Based on the information received from the peak value calculation unit 35-1, the trend analysis unit 35-2 may analyze a trend of the changes of the peak value according to the changes in the focal length of the SEM 10.

Analyzing the trend of the changes of the peak value according to the changes in the focal length of the SEM 10 may include, for example, calculating a focal length of the SEM 10 which makes the peak value have a maximum value.

By analyzing characteristics of gray-level histograms as described above, a focal length of the SEM 10 when the focus of the SEM 10 is formed on the surface of an inspection target can be calculated. Specifically, when the focus of the SEM 10 is formed on the surface of an inspection target, a clearest SEM image can be obtained, and the contrast of this SEM image may be highest. Therefore, if SEM images captured by varying the focal length of the SEM 10 are converted into gray-level histograms and then the gray-level histograms are analyzed, it can be identified that a gray-level histogram for a SEM image captured when the focus of the SEM 10 is formed on the surface of an inspection target has a relatively narrowest distribution. In addition, a gray-level value and a frequency value corresponding to a peak of the gray-level histogram when the focus of the SEM 10 is formed on the surface of the inspection target are relatively highest.

Therefore, a focal length of the SEM 10 which makes the peak value have the maximum value can be calculated by analyzing the trend of the changes in the peak value according to the changes in the focal length of the SEM 10. In addition, when the calculated focal length of the SEM 10 is applied, it can be understood that the focus of the SEM 10 is formed on the surface of an inspection target.

The step height determination unit 37 may be a portion of the SEM image processor 30 which receives an analysis result from the trend analysis unit 35-2 and determines a height of a step formed in an inspection target based on the received analysis result. For example, if a step has a top surface and a bottom surface, the step height determination unit 37 may receive from the trend analysis unit 35-2 information about a first focal length which makes the focus of the SEM 10 be formed on the top surface of the step and a second focal length which makes the focus of the SEM 10 be formed on the bottom surface of the step. The step height determination unit 37 may determine a difference between the first focal length and the second focal length to be the height of the step. That is, since the position of the electromagnetic lens of the SEM 10 is fixed, the difference between the first focal length which is the distance from the electromagnetic lens to the top surface of the step and the second focal length which is the distance from the electromagnetic lens to the bottom surface of the step may be equal to the height of the step.

The step height measuring apparatus 1 according to the present embodiment can measure a 3D depth by analyzing the SEM image 200 which is a 2D image. In addition, since information about depth or height can be obtained using the step height measuring apparatus 1, a 3D shape of an inspection target can be obtained. Furthermore, the use of the SEM 10 negates the need for additional equipment for measuring a 3D depth or a 3D shape, thus reducing costs.

The SEM 10 has high resolution and can extract the SEM image 200 of a fine pattern without being limited by the repeatability or shape of the fine pattern. In addition, since the SEM 10 uses a non-contact scanning method, a reduction in measurement reliability due to an increase in the number of times that measurement is conducted can be prevented.

Figure 2:
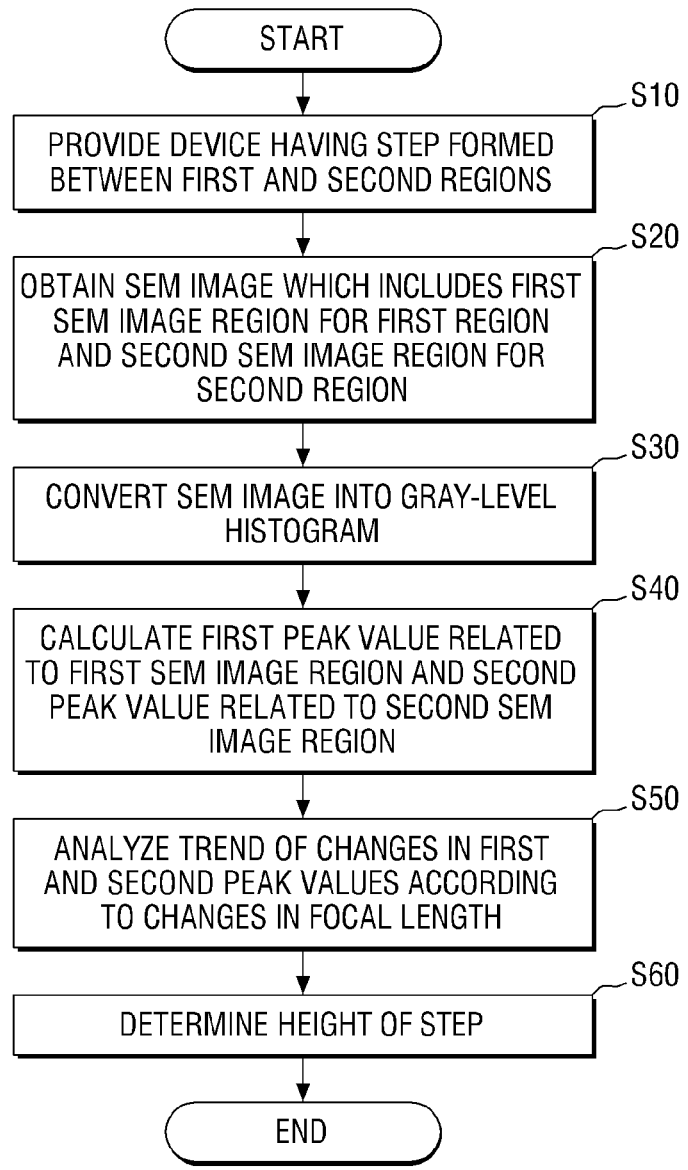
FIG. 2 is a flowchart illustrating a method of measuring a step height according to exemplary embodiments of the present inventive concept.
Figure 3:
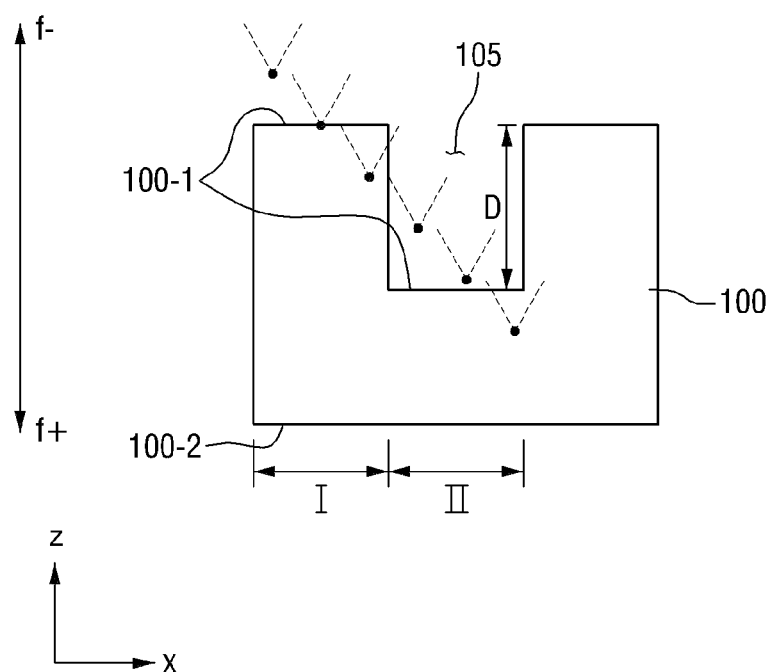
FIG. 3 is a cross-sectional view of a device, illustrating the step height measuring method according to the embodiments of FIG. 2.
Figure 4:
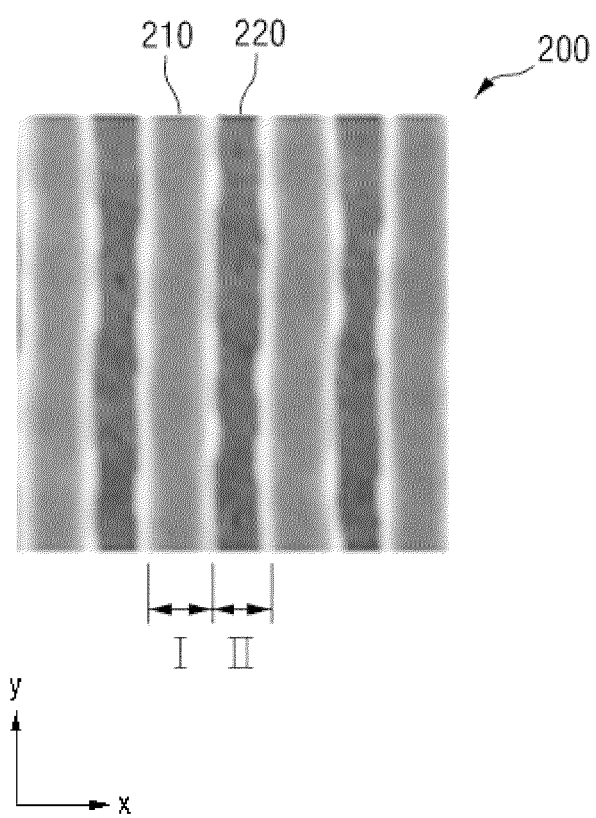
FIG. 4 is a scanning electron microscope (SEM) image of the device shown in FIG. 3.
Figure 5:
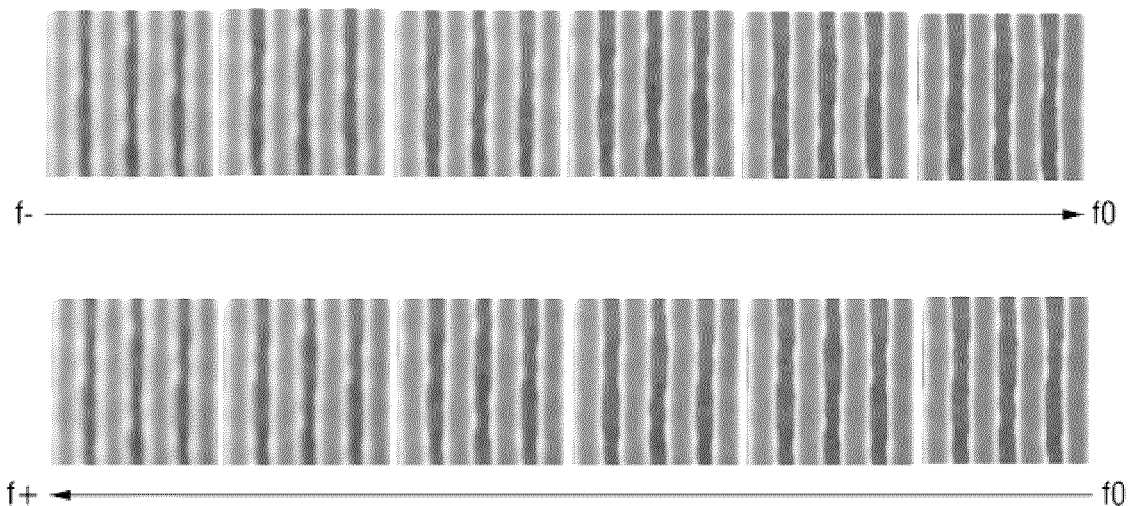
FIG. 5 shows SEM images of the device of FIG. 3 captured by varying a focal length of a SEM.
Figure 6:
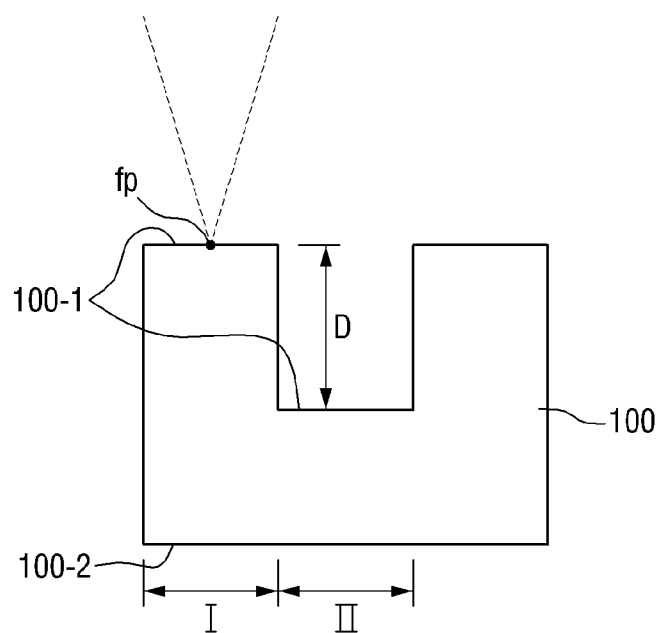
FIG. 6 is a cross-sectional view of the device having a focus of the SEM formed on a top surface of a first region thereof.
Figure 7:
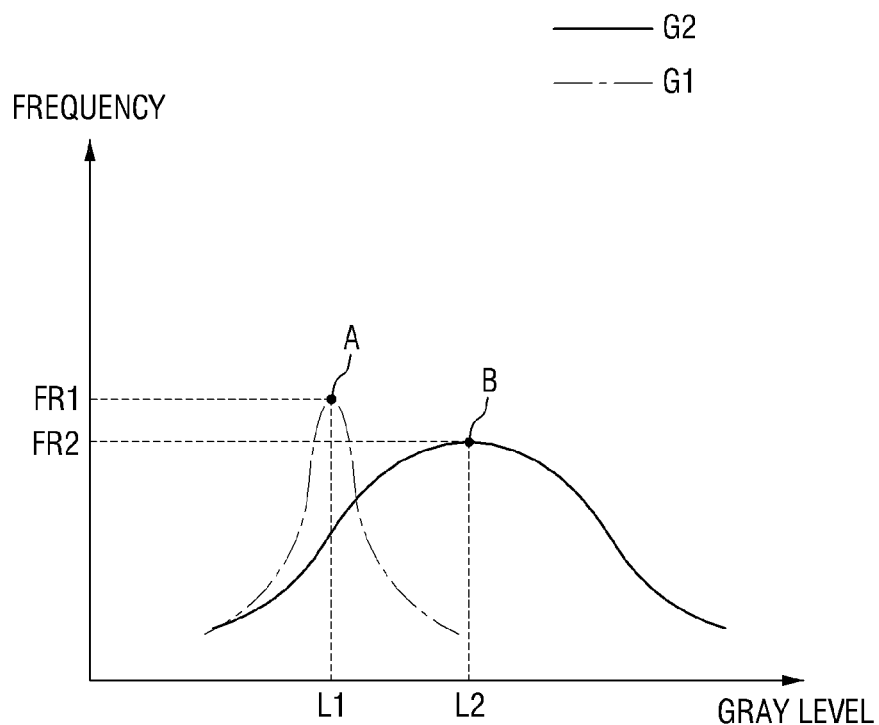
FIG. 7 is a gray-level histogram for a SEM image captured under the conditions of FIG. 6.
Figure 8:
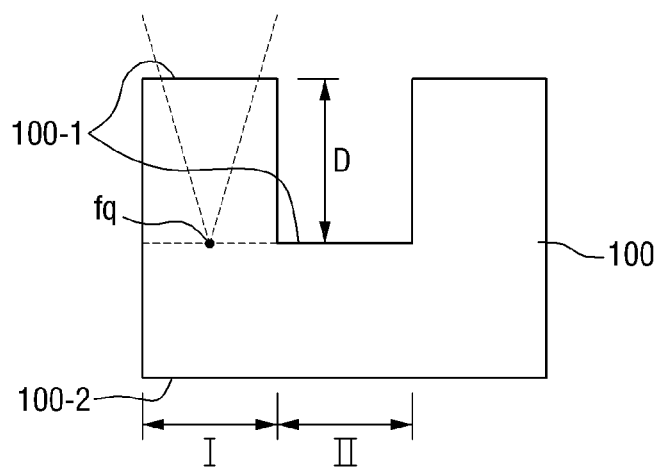
FIG. 8 is a cross-sectional view of the device having the focus of the SEM formed on a top surface of a second region thereof.
Figure 9:
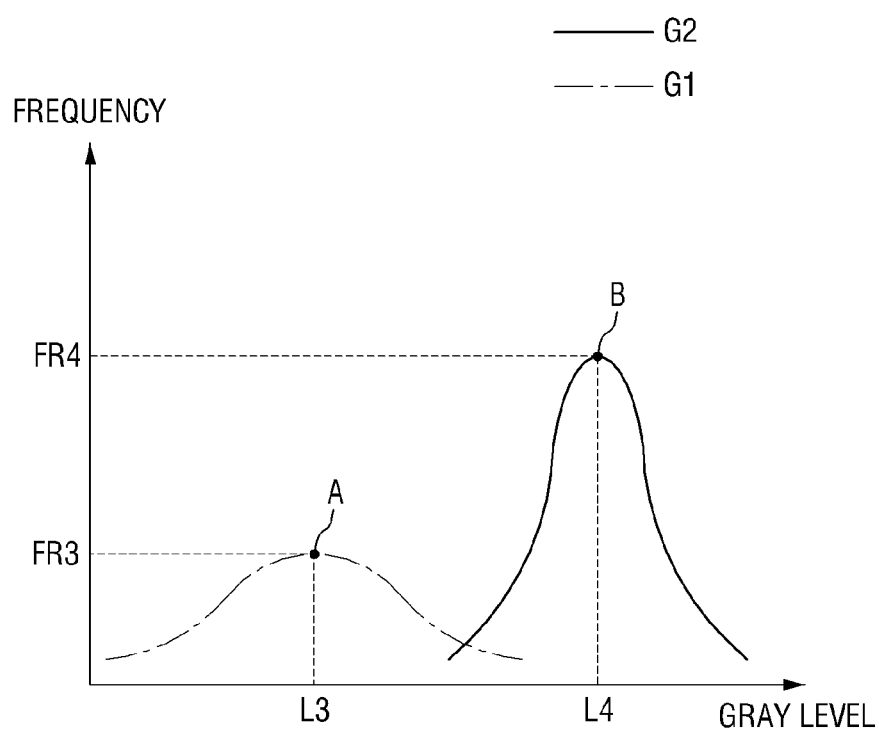
FIG. 9 is a gray-level histogram for a SEM image captured under the conditions of FIG. 8.
Figure 10:
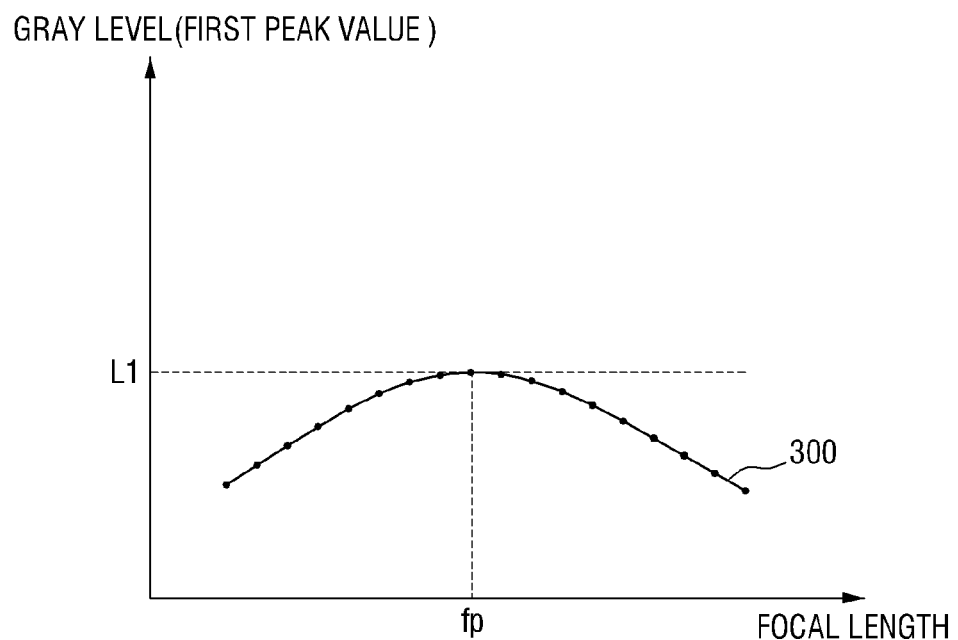
FIG. 10 is a graph showing a trend of changes in a first peak value according to changes in the focus of the SEM, in the step height measuring method according to an embodiment of the present inventive concept.
Figure 11:
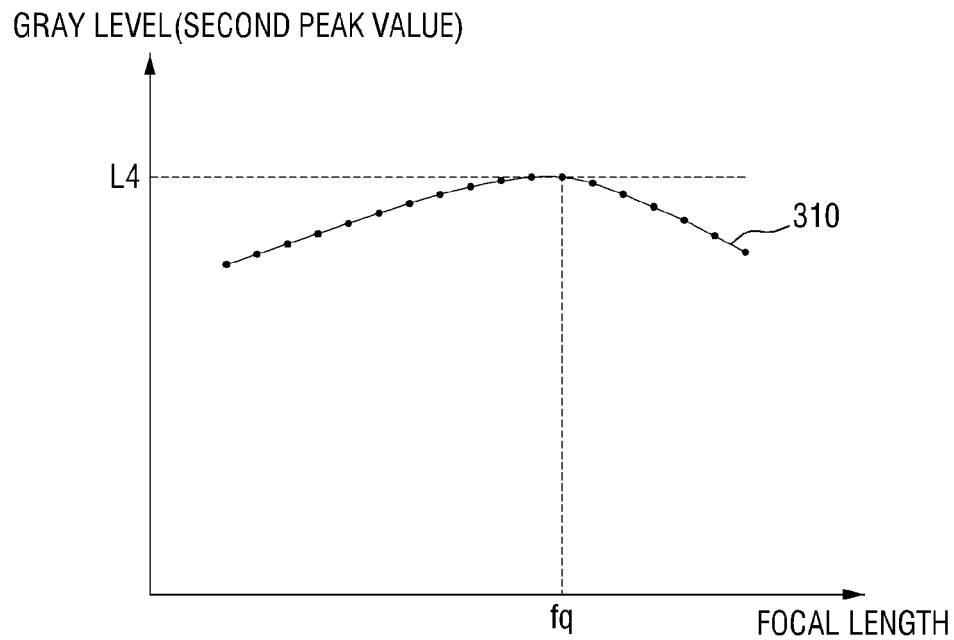
FIG. 11 is a graph showing a trend of changes in a second peak value according to changes in the focus of the SEM, in the step height measuring method according to the embodiment of FIG. 10.
Figure 12:
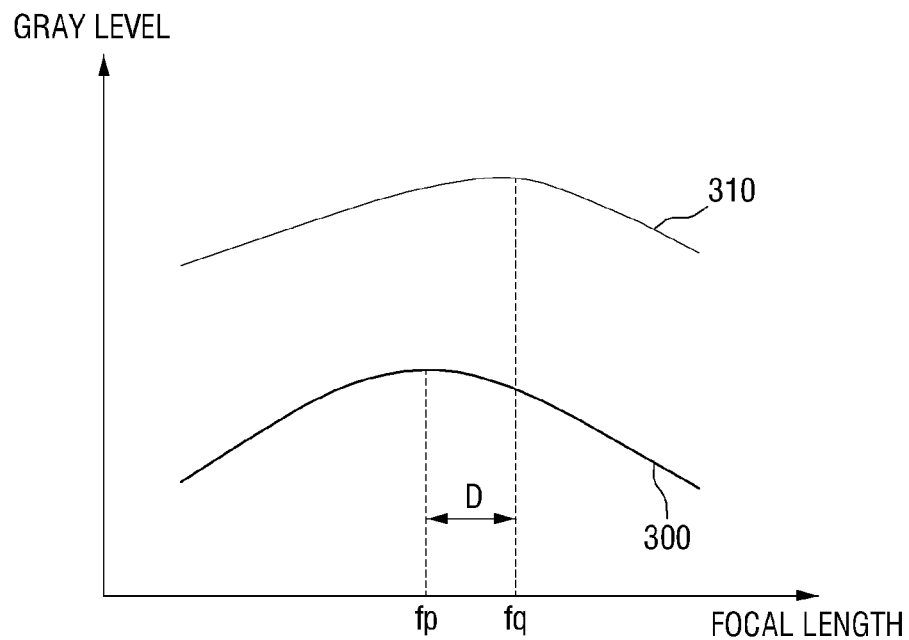
FIG. 12 is a graph illustrating a method of determining a step height in the step height measuring method according to the embodiment of FIG. 10.

A method of measuring a step height of a device using a SEM according to an embodiment of the present inventive concept will now be described with reference to FIGS. 2 through 12. FIG. 2 is a flowchart illustrating a method of measuring a step height according to the embodiments of the present inventive concept. FIG. 3 is a cross-sectional view of a device, illustrating the step height measuring method according to the embodiment of FIG. 2. FIG. 4 is a SEM image of the device shown in FIG. 3. FIG. 5 shows SEM images of the device of FIG. 3 captured by varying a focal length of a SEM. FIG. 6 is a cross-sectional view of the device having a focus of the SEM formed on a top surface of a first region thereof. FIG. 7 is a gray-level histogram for a SEM image captured under the conditions of FIG. 6. FIG. 8 is a cross-sectional view of the device having the focus of the SEM formed on a top surface of a second region thereof. FIG. 9 is a gray-level histogram for a SEM image captured under the conditions of FIG. 8. FIG. 10 is a graph showing a trend of changes in a first peak value according to changes in the focus of the SEM, in the step height measuring method according to an embodiment of the present inventive concept. FIG. 11 is a graph showing a trend of changes in a second peak value according to changes in the focus of the SEM, in the step height measuring method according to the embodiment of FIG. 10. FIG. 12 is a graph illustrating a method of determining a step height in the step height measuring method according to the embodiment of FIG. 10.

Referring to FIGS. 2 and 3, a device 100 may be provided (operation S10). The device 100 may include a first region I and a second region II, and a step may be formed between the first region I and the second region II.

The device 100 can be understood as a sample. The device 100 may be, but is not limited to, a semiconductor-type wafer, or other devices used in semiconductor manufacturing. A step may be formed in the device 100. For example, an etch pattern may be formed in the device 100 as a result of an etch process. A trench, groove or hole may be formed in an etched region of the device 100. Therefore, the etched region of the device 100 may be different in height from a relatively less etched region or an un-etched region. The step formed in the device 100 may not necessarily be a result of the etch process.

Specifically, a step may be formed between the first region I and the second region II of the device 100. The first region I may be a relatively less etched region or an un-etched region, and the second region II may be a relatively more etched region. In FIG. 3, a trench 105 is formed in the second region II. Therefore, a height D of the step may be substantially equal to an etch depth of the device 100.

The device 100 may have a top surface 100-1 and a bottom surface 100-2. Since the trench 105 is formed in the second region II, the position of the top surface 100-1 of the second region II may be different from that of the top surface 100-1 of the first region I. For example, the top surface 100-1 of the second region II may be, but is not limited to, relatively lower than the top surface 100-1 of the first region I.

Referring to FIGS. 2 through 5, a SEM image 200 of the device 100 is obtained by photographing the device 100 using the SEM 10. The SEM image 200 may include a first SEM image region 210 for the first region I and a second SEM image region 220 for the second region II (operation S20).

Specifically, referring to FIGS. 3 and 4, the SEM image 200 may be obtained by photographing the top surface 100-1 of the device 100 using the SEM 10. The SEM image 200 may include the first SEM image region 210 obtained by photographing the top surface 100-1 of the first region I of the device 100 and the second SEM image region 220 obtained by photographing the top surface 100-1 of the second region II of the device 100.

Photographing the device 100 using the SEM 10 may be performed multiple times by varying the focal length of the SEM 10. In FIG. 3, positions at which the focus of the SEM 10 is formed are illustrated by way of example. Since the electromagnetic lens of the SEM 10 can be placed above the device 100, the focal length of the SEM 10 may be reduced (f−) such that the focus of the SEM 10 is formed close to the electromagnetic lens placed above the device 100. That is, as the focus of the SEM 10 is formed further away from the bottom surface 100-2 of the device 100, the focal length of the SEM 10 may decrease (f−). Conversely, as the focus of the SEM 10 is formed closer to the bottom surface 100-2 of the device 100, the focal length of the SEM 10 may increase (f+).

In the step height measuring method according to the current embodiment of the present inventive concept, if a SEM image captured when the focus of the SEM 10 is formed precisely on the top surface 100-1 of the first region I and a SEM image captured when the focus of the SEM 10 is formed precisely on the top surface 100-1 of the second region II are obtained, the reliability of step height measurement can be increased.

The focal length of the SEM 10 can be changed by the SEM controller 20. In addition, SEM images 200 captured by varying the focal length of the SEM 10 multiple times can be obtained by the SEM image acquisition unit 31. Here, a difference between a maximum focal length and a minimum focal length may be greater than a height D of a step.

In the step height measuring method according to the current embodiment of the present inventive concept, since the device 100 is photographed by varying the focal length of the SEM 10, SEM images 200 for various focal lengths can be obtained. Referring to FIG. 5, as the focal length of the SEM 10 varies, the contrast of the SEM image 200 may also vary. A change in the contrast of the SEM image 200 may be understood as a change in the sharpness of the SEM image 200. For example, when the focus of the SEM 10 is formed on the top surface 100-1 of the first region I, the contrast of the first SEM image region 210 may increase. As a result, the first SEM image region 210 may become clearer. Likewise, when the focus of the SEM 10 is formed on the top surface 100-1 of the second region II, the contrast of the second SEM image region 220 may increase. As a result, the second SEM image region 220 may become clearer.

Therefore, a position at which the focus of the SEM 10 was formed can be calculated by analyzing a SEM image 200. For example, a SEM image 200 which includes the first SEM image region 210 with highest sharpness can be found by examining each SEM image 200 of FIG. 5. In addition, the fact that the focus of the SEM 10 was formed on the top surface 100-1 of the first region I of the device 100 when the found SEM image 200 was captured means that a first focal length of the SEM 10 at this time can be identified.

Likewise, a SEM image 200 which includes the second SEM image region 220 with highest sharpness can be found by examining each SEM image 200 of FIG. 5. In addition, the fact that the focus of the SEM 10 was formed on the top surface 100-1 of the second region II of the device 100 when the found SEM image 200 was captured and means that a second focal length of the SEM 10 at this time can be identified.

Subsequently, the SEM image 200 may be converted into a gray-level histogram in order to determine the sharpness of each of the first and second SEM image regions 210 and 220.

Referring to FIGS. 2 and 6 through 9, the SEM image 200 may be converted into a gray-level histogram (operation S30).

Specifically, the histogram generation unit 33 may convert the SEM image 200 into a gray-level histogram. Referring to FIGS. 7 through 9, a gray level of a brightness value of each pixel in the SEM image 200 was converted into a numerical value, and the frequency of each gray level was plotted on a graph. FIG. 7 is a gray-level histogram for a SEM image 200 captured when the focus of the SEM 10 was formed on the top surface 100-1 of the first region I of the device 100. FIG. 9 is a gray-level histogram for a SEM image 200 captured when the focus of the SEM 10 was formed on the top surface 100-1 of the second region II of the device 100. Therefore, the gray-level histograms of FIGS. 7 and 9 may be different.

A first graph G1 is a gray-level histogram for the first SEM image region 210, and a second graph G2 is a gray-level histogram for the second SEM image region 220. In FIGS. 7 and 9, the gray-level histograms for the first and second SEM image regions 210 and 220 are represented by the first and second graphs G1 and G2, respectively. However, the present inventive concept is not limited thereto. One gray-level histogram may be generated for the SEM image 200 without differentiating between the first and second SEM image regions 210 and 220.

Referring to FIGS. 2 and 6 through 9, a first peak value related to the first SEM image region 210 and a second peak value related to the second SEM image region 220 may be calculated (operation S40). The calculating of the first and second peak values may be repeated as the focal length of the SEM 10 changes.

Referring to FIGS. 7 and 9, the peak value calculation unit 35-1 may calculate a peak value based on a gray-level histogram. Specifically, the peak value calculation unit 35-1 may calculate the first peak value corresponding to a peak A of the first graph G1. The first peak value may be a gray-level value (L1, L3) corresponding to the peak A related to the first SEM image region 210.

In addition, the peak value calculation unit 35-1 may calculate the second peak value corresponding to a peak B of the second graph G2. The second peak value may be a gray-level value (L2, L4) corresponding to the peak B related to the second SEM image region 220.

Whenever the focal length of the SEM 10 is changed, a new SEM image 200 may be obtained. Accordingly, a new gray-level histogram may be generated. Therefore, whenever the focal length of the SEM 10 is changed, the first and second peak values may be newly calculated according to the changed focal length of the SEM 10. The peak value calculation unit 35-1 may provide the trend analysis unit 35-2 with information about the first and second peak values with respect to the focal length of the SEM 10.

The change in the first and second peak values and the first and second graphs G1 and G2 according to the change in the focal length of the SEM 10 will now be described with reference to FIGS. 6 through 9. FIG. 7 is a gray-level histogram for a SEM image 200 captured when the focal length of the SEM 10 was fp and when the focus of the SEM 10 was formed on the top surface 100-1 of the first region I of the device 100 as shown in FIG. 6. Since the focus of the SEM 10 is formed on the top surface 100-1 of the first region I of the device 100, the contrast of the first SEM image region 210 may be relatively high. On the other hand, FIG. 9 is a gray-level histogram for a SEM image 200 captured when the focal length of the SEM 10 was fp and when the focus of the SEM 10 was formed on the top surface 100-1 of the second region II of the device 100 as shown in FIG. 8. Since the focus of the SEM 10 is separated from the top surface 100-1 of the first region I, the contrast of the first SEM image region 210 may be relatively low.

Therefore, a peak width of the first graph G1 of FIG. 7 (related to the first SEM image region 210) may be narrower than that of the first graph G1 of FIG. 9. In addition, the first peak value L1 of the first graph G1 of FIG. 7 may be higher than the first peak value L3 of the first graph G1 of FIG. 9.

Conversely, a peak width of the second graph G2 of FIG. 9 (related to the second SEM image region 220) may be narrower than that of the second graph G2 of FIG. 7. In addition, the second peak value L4 of the second graph G2 of FIG. 9 may be higher than the second peak value L2 of the second graph G2 of FIG. 7.

Referring to FIGS. 2, 10 and 11, a trend of changes in the first peak value according to changes in the focal length and a trend of changes in the second peak value according to changes in the focal length may be analyzed (operation S50).

Referring to FIG. 10, the trend analysis unit 35-2 may produce a first trend graph 300 of the first peak value with respect to the focal length of the SEM 10. That is, the first trend graph 300 illustrates the correlation between a change in the focal length of the SEM 10 and a change in the first peak value (gray level).

The trend analysis unit 35-2 may calculate a first focal length that makes the first peak value have a maximum value by analyzing the first trend graph 300. For example, the trend analysis unit 35-2 may calculate the first focal length by reflecting the result of differentiating the trend of changes in the first peak value according to changes in the focal length with respect to the focal length. Specifically, a point at which a derivative is zero may be found, and a focal length corresponding to the point at which the derivative is zero may be determined to be the first focal length.

For example, the point at which the derivative is zero may be a point at which the focal length is fp and a gray-level value is L1. The point at which the focal length is fp and the gray-level value is L1 may correspond to a case where the focus of the SEM 10 is formed on the top surface 100-1 of the first region I of the device 100. Therefore, the first focal length which makes the first peak value have the maximum value may be equal to the distance from the electromagnetic lens of the SEM 10 to the top surface 100-1 of the first region I of the device 100.

Referring to FIG. 11, the trend analysis unit 35-2 may produce a second trend graph 310 of the second peak value with respect to the focal length of the SEM 10. That is, the second trend graph 300 illustrates the correlation between a change in the focal length of the SEM 10 and a change in the second peak value (gray level).

The trend analysis unit 35-2 may calculate a second focal length that makes the second peak value have a maximum value by analyzing the second trend graph 310. For example, the trend analysis unit 35-2 may calculate the second focal length by reflecting the result of differentiating the trend of changes in the second peak value according to changes in the focal length with respect to the focal length. Specifically, a point at which a derivative is zero may be found, and a focal length corresponding to the point at which the derivative is zero may be determined to be the second focal length.

For example, the point at which the derivative is zero may be a point at which the focal length is fq and a gray-level value is L4. The point at which the focal length is fq and the gray-level value is L4 may correspond to a case where focus of the SEM 10 is formed on the top surface 100-1 of the second region II of the device 100. Therefore, the first focal length which makes the second peak value have the maximum value may be equal to the distance from the electromagnetic lens of the SEM 10 to the top surface 100-1 of the second region IL of the device 100.

Referring to FIGS. 2 and 12, a height D of a step may be determined (operation S60).

Referring to FIG. 12, the step height determination unit 37 may calculate a difference between the first focal length calculated through the analysis of the first trend graph 300 and the second focal length calculated through the analysis of the second trend graph 310 and determine the distance between the first focal length and the second focal length to be the height D of the step.

That is, the first focal length may be equal to the distance from the electromagnetic lens of the SEM 10 to the top surface 100-1 of the first region I of the device 100, and the second focal length may be equal to the distance from the electromagnetic lens of the SEM 10 to the top surface 100-1 of the second region II of the device 100. In this case, the difference between the first focal length and the second focal length may be equal to a distance between the top surface 100-1 of the first region I of the device 100 and the top surface 100-1 of the second region II of the device 100. Therefore, the difference between the first focal length and the second focal length may be equal to the height D of the step.

Figure 13:
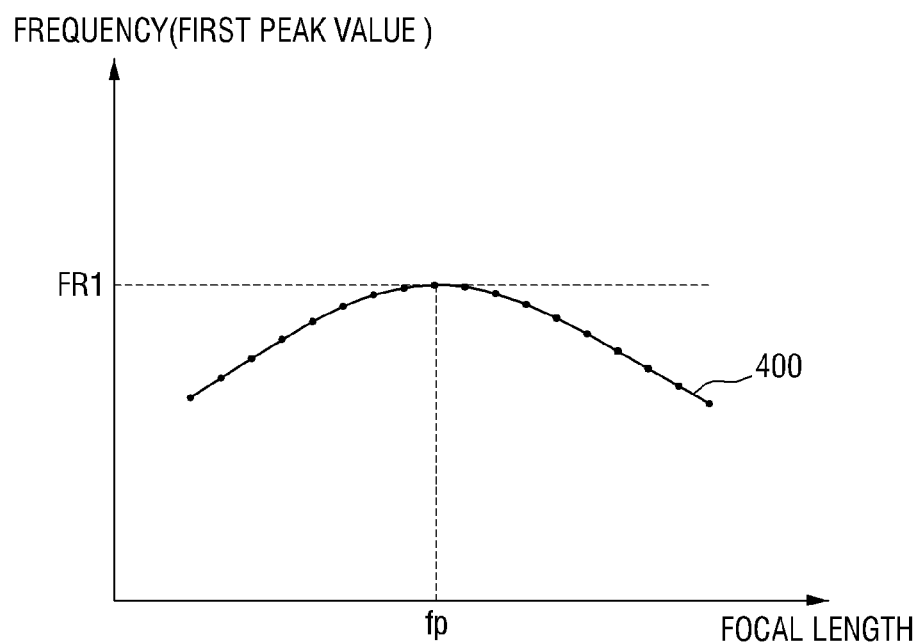
FIG. 13 is a graph showing a trend of changes in a first peak value according to changes in a focus of a SEM, in a method of measuring a step height according to another embodiment of the present inventive concept.
Figure 14:
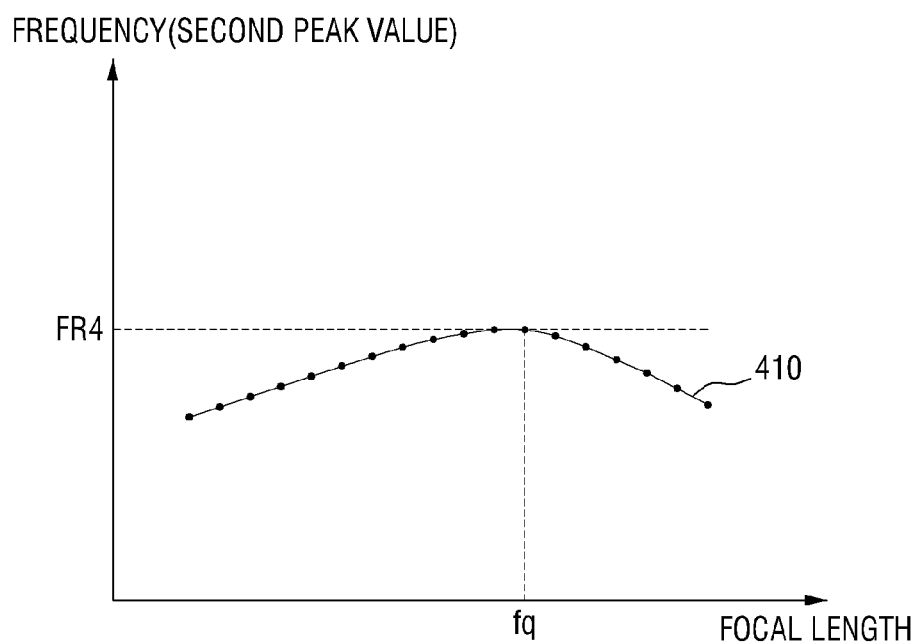
FIG. 14 is a graph showing a trend of changes in a second peak value according to changes in the focus of the SEM, in the step height measuring method according to the embodiment of FIG. 13.
Figure 15:
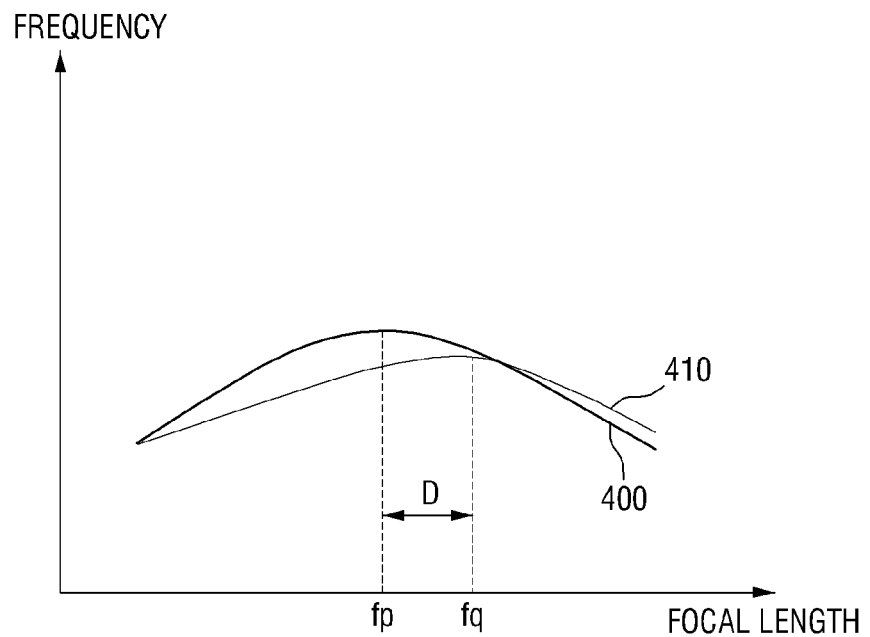
FIG. 15 is a graph illustrating a method of determining a step height in the step height measuring method according to the embodiment of FIG. 13.

A method of measuring a step height of a device using a SEM according to another embodiment of the present inventive concept will now be described with reference to FIGS. 13 through 15. For simplicity, the following description will focus on differences from the step height measuring method according to the previous embodiment of the present inventive concept. FIG. 13 is a graph showing a trend of changes in a first peak value according to changes in a focus of a SEM, in a method of measuring a step height according to another embodiment of the present inventive concept. FIG. 14 is a graph showing a trend of changes in a second peak value according to changes in the focus of the SEM, in the step height measuring method according to the embodiment of FIG. 13. FIG. 15 is a graph illustrating a method of determining a step height in the step height measuring method according to the embodiment of FIG. 13.

Referring to FIGS. 13 through 15, in the step height measuring method according to the current embodiment of the present inventive concept, frequency values may be used as first and second peak values. Specifically, the first peak value may be a frequency value (FR1, FR3) corresponding to a peak A related to a first SEM image region 210, and the second peak value may be a frequency value (FR2, FR4) corresponding to a peak B related to a second SEM image region 220. Therefore, a height D of a step can be determined by analyzing a third trend graph 400 and a fourth trend graph 410.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims. It is therefore desired that the present embodiments be considered in all respects as illustrative and not restrictive, reference being made to the appended claims rather than the foregoing description to indicate the scope of the inventive concept.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

What is claimed is:

1. A method of measuring a step height of a device using a scanning electron microscope (SEM), the method comprising:
   providing a device which comprises a first region and a second region, wherein a step is formed between the first region and the second region;
   obtaining a plurality of SEM images of the device at varying focal lengths by photographing the device using a SEM, wherein the SEM image comprises a first SEM image region for the first region and a second SEM image region for the second region;
   converting the SEM images into a gray-level histogram and calculating a first peak value related to the first SEM image region and a second peak value related to the second SEM image region, wherein the first peak value and the second peak value are repeatedly calculated at varying focal lengths of the SEM; and
   determining a height of the step by analyzing a trend of changes in the first peak value according to changes in the focal length and a trend of changes in the second peak value according to the changes in the focal length.

2. The method of claim 1, wherein the first peak value is a gray-level value corresponding to a peak related to the first SEM image region in the gray-level histogram, and the second peak value is a gray-level value corresponding to a peak related to the second SEM image region in the gray-level histogram.

3. The method of claim 1, wherein the first peak value is a frequency value corresponding to the peak related to the first SEM image region in the gray-level histogram, and the second peak value is a frequency value corresponding to the peak related to the second SEM image region in the gray-level histogram.

4. The method of claim 1, wherein the analyzing of the trend of the changes in the first peak value according to the changes in the focal length and the trend of the changes in the second peak value according to the changes in the focal length comprises calculating a first focal length which makes the first peak value have a maximum value by analyzing the trend of the changes in the first peak value according to the changes in the focal length and calculating a second focal length which makes the second peak value have a maximum value by analyzing the trend of the changes in the second peak value according to the changes in the focal length.

5. The method of claim 4, wherein the determining of the height of the step comprises determining a difference between the first focal length and the second focal length to be the height of the step.

6. The method of claim 4, wherein the calculating of the first focal length which makes the first peak value have the maximum value comprises calculating the first focal length by reflecting a result of differentiating the trend of the changes in the first peak value according to the changes in the focal length with respect to the focal length, and the calculating of the second focal length which makes the second peak value have the maximum value comprises calculating the second focal length by reflecting a result of differentiating the trend of the changes in the second peak value according to the changes in the focal length with respect to the focal length.

7. The method of claim 1, wherein the varying of the focal length of the SEM comprises varying the focal length of the SEM multiple times, and a difference between a maximum focal length and a minimum focal length is greater than the height of the step.

8. The method of claim 1, wherein the device comprises a top surface and a bottom surface which are opposite each other, the SEM image is an image of the top surface of the device, the first SEM image region is an image of a top surface of the first region, and the second SEM image region is an image of a top surface of the second region.

9. The method of claim 1, wherein the second region is an etched region of the device, and the height of the step is substantially equal to an etch depth of the device.

10. An apparatus for measuring a height of a step formed between a first region and a second region of a device by using a SEM, the apparatus comprising:
   a SEM image acquisition unit obtaining a SEM image which comprises a first SEM image region for the first region and a second SEM image region for the second region, wherein the SEM image is repeatedly captured by varying a focal length of the SEM multiple times;
   a histogram generation unit converting the SEM image into a gray-level histogram;
   a peak value calculation unit calculating a first peak value related to the first SEM image region and a second peak value related to the second SEM image region by analyzing the gray-level histogram;
   a trend analysis unit analyzing a trend of changes in the first peak value according to changes in the focal length and a trend of changes in the second peak value according to the changes in the focal length; and
   a step height determination unit receiving an analysis result from the trend analysis unit and determining the height of the step.

11. The apparatus of claim 10, wherein the first peak value is a gray-level value corresponding to a peak related to the first SEM image region in the gray-level histogram, and the second peak value is a gray-level value corresponding to a peak related to the second SEM image region in the gray-level histogram.

12. The apparatus of claim 10, wherein the first peak value is a frequency value corresponding to the peak related to the first SEM image region in the gray-level histogram, and the second peak value is a frequency value corresponding to the peak related to the second SEM image region in the gray-level histogram.

13. The apparatus of claim 10, wherein the analyzing of the trend of the changes in the first peak value according to the changes in the focal length and the trend of the changes in the second peak value according to the changes in the focal length comprises calculating a first focal length which makes the first peak value have a maximum value by analyzing the trend of the changes in the first peak value according to the changes in the focal length and calculating a second focal length which makes the second peak value have a maximum value by analyzing the trend of the changes in the second peak value according to the changes in the focal length.

14. The apparatus of claim 13, wherein the determining of the height of the step comprises determining a difference between the first focal length and the second focal length to be the height of the step.

15. The apparatus of claim 10, wherein a difference between a maximum focal length and a minimum focal length is greater than the height of the step.

16. A method of measuring a step height of a device using a scanning electron microscope (SEM), the method comprising:
   obtaining a plurality of SEM images of a device at varying focal lengths by photographing the device using an SEM, wherein the SEM image comprises a first SEM image region for a first region of the device and a second SEM image region for a second region of the device;
   calculating a first peak value related to the first SEM image region and a second peak value related to the second SEM image region, wherein the first peak value and the second peak values are repeatedly calculated at varying focal lengths of the SEM; and
   determining a difference in height between the first region and the second region by analyzing a trend of changes in the first peak value according to changes in the focal length and a trend of changes in the second peak value according to the changes in the focal length.

17. The method of claim 16, further comprising:
   converting the obtained SEM image into a gray-level histogram,
   wherein the first peak value is a gray-level value corresponding to a peak related to the first SEM image region in the gray-level histogram, and the second peak value is a gray-level value corresponding to a peak related to the second SEM image region in the gray-level histogram.

18. The method of claim 16, further comprising:
   converting the obtained SEM image into a gray-level histogram,
   wherein the first peak value is a frequency value corresponding to the peak related to the first SEM image region in the gray-level histogram, and the second peak value is a frequency value corresponding to the peak related to the second SEM image region in the gray-level histogram.

19. The method of claim 18, wherein the first region of the device is stepped with respect to the second region of the device.

* * * * *